United States Patent
Jansen et al.

(10) Patent No.: US 7,069,072 B2
(45) Date of Patent: Jun. 27, 2006

(54) METHOD AND DEVICE FOR DETERMINING THE SEGMENTAL VOLUME AND ELECTRICAL PARALLEL CONDUCTANCE OF A CARDIAC CHAMBER OR BLOOD VESSEL

(75) Inventors: Jozef R. C. Jansen, Aster 8, N1-2211 MZ, Noordwijkerhout (NL); Johannes Jacobus Schreuder, Varese (IT)

(73) Assignee: Jozef R. C. Jansen, Noordwijkerhout (NL)

( * ) Notice: Subject to any disclaimer, the term of this patent is extended or adjusted under 35 U.S.C. 154(b) by 237 days.

(21) Appl. No.: 10/363,713

(22) PCT Filed: Aug. 30, 2001

(86) PCT No.: PCT/NL01/00641

§ 371 (c)(1),
(2), (4) Date: Aug. 28, 2003

(87) PCT Pub. No.: WO02/19905

PCT Pub. Date: Mar. 14, 2002

(65) Prior Publication Data

US 2004/0024329 A1 Feb. 5, 2004

(30) Foreign Application Priority Data

Sep. 7, 2000 (NL) .................................. 1016122

(51) Int. Cl.
*A61B 5/00* (2006.01)

(52) U.S. Cl. ........................ 600/547; 600/505; 600/526

(58) Field of Classification Search ..................... None
See application file for complete search history.

(56) References Cited

U.S. PATENT DOCUMENTS

| 4,380,237 A |   | 4/1983 | Newbower ................... 128/693 |
|---|---|---|---|
| 4,674,518 A | * | 6/1987 | Salo ........................... 600/508 |
| 4,721,115 A | * | 1/1988 | Owens ........................ 600/526 |
| 4,840,182 A | * | 6/1989 | Carlson ....................... 600/507 |

(Continued)

FOREIGN PATENT DOCUMENTS

EP        0 092 438        10/1983

(Continued)

OTHER PUBLICATIONS

"Continous stroke volume and cardiac output from intraventricular dimensions obtained with impedance catheter", J. Baan et al., Vardiovascular Research, vol. 15, 1981, pp. 328-334.

(Continued)

*Primary Examiner*—Robert L. Nasser, Jr.
(74) *Attorney, Agent, or Firm*—Steven M. Koehler; Westman, Champlin & Kelly, P.A.

(57) ABSTRACT

The segment volume of a cardiac chamber or blood vessel of a patient is determined by injecting a first indicator in the blood stream of a patient, which influences the conductance of the blood. The electrical conductance in the cardiac chamber or blood vessel is measured. An injected quantity of indicator is determined and the development of the concentration of this indicator in the blood is measured wherein the cardiac output is calculated from the injected quantity of indicator and the development of the concentration in the blood. Subsequently, the segment volume and electrical parallel conductance of a cardiac chamber or blood vessel are calculated from the calculated cardiac output, the injected quantity of conductance indicator and the measured conductance.

16 Claims, 3 Drawing Sheets

U.S. PATENT DOCUMENTS 5,000,190 A * 3/1991 Petre .......................... 600/526
5,092,339 A * 3/1992 Geddes et al. ............. 600/505
5,882,312 A * 3/1999 Gopakumaran et al. .... 600/526

FOREIGN PATENT DOCUMENTS

| NL | 1005572 | 9/1998 |
|----|---------|--------|
| WO | WO 89/12421 | 12/1989 |
| WO | WO 93/13823 | 7/1993 |

OTHER PUBLICATIONS

J. Baan, et al., Calibration and Application of the Conductance Catheter For Ventricular Volume Measurement, Automedica 1989, vol. 11, pp. 357-365.

* cited by examiner

METHOD AND DEVICE FOR DETERMINING THE SEGMENTAL VOLUME AND ELECTRICAL PARALLEL CONDUCTANCE OF A CARDIAC CHAMBER OR BLOOD VESSEL

CROSS-REFERENCE TO RELATED APPLICATION

This Application is a Section 371 National Stage Application of International Application No. PCT/NL01/00641, filed 30 Aug. 2001 and published as WO 02/19905 on 14 Mar. 2002 in English.

BACKGROUND OF THE INVENTION

The invention relates to a method for determining the segmental volume and the electrical parallel conductance of a cardiac chamber or a blood vessel of a patient, wherein a first indicator, which influences the conductance of the blood, is injected into the bloodstream of a patient, wherein the electrical conductance in said cardiac chamber or blood vessel is measured and wherein the sum of the segmental volume of said cardiac chamber or blood vessel and the electrical parallel conductance is calculated from said conductance, as well as to an apparatus for determining the segmental volume of a cardiac chamber or a blood vessel of a patient and to a catheter for use in said method or apparatus.

Such a method and apparatus are known from the article of Baan et al in Automedica 1989, vol. 11, pp. 357–365. A so-called electrical conductance method can be carried out therewith, wherein a catheter is introduced into one of the cardiac chambers of a patient. Said catheter, which comprises several annular electrodes, provides a signal which is a measure of the sum of the electrical conductance of the blood in the cardiac chamber and the electrical conductance of the structures surrounding the blood in the cardiac chamber, which is called parallel conductance. With regard to this overall conductance the following holds true:

$$G(t) = Q(t) \cdot \frac{\sigma_b}{L^2} + G_p \qquad (1)$$

wherein $Q(t)$ is the volume in the cardiac chamber, $L$ is the spacing between the annular electrodes, $\sigma_b$ is the electrical conductivity of blood, $G(t)$ is the sum of the measured electrical conductance values between the successive annular electrodes, and $G_p$ is the associated parallel conductance. Parallel conductance $G_p$ is assumed to be constant. The determination of the parallel conductance is based on the linear relation between the measured conductance $G(t)$ and the conductivity of the blood $\sigma_b$. The conductivity of the blood is changed by means of an injection of a hypertonic saline solution (0.8 M/l, 5–10 ml for humans) or a hypotonic glucose solution (glucose solution 10 ml) upstream of the catheter, for example in the pulmonary artery. The parallel conductance is determined by plotting the measured conductance at minimum chamber volume ($G_{minimum}$) at the beginning of the filling stage against the measured conductance at maximum chamber volume ($G_{maximum}$) at the beginning of the ejection stage. These values are determined heartbeat after heartbeat during the increasing (or decreasing) conductivity of the blood following the injection of the saline solution (or glucose solution). The linear regression line through said values is extrapolated to the identity line, wherein the value in the point of intersection is considered to be the value of the parallel conductance. Since this method employs extrapolation of the relation between ($G_{minimum}$) and ($G_{maximum}$) to the identity line for only a small number of heartbeats, a small error in the determination of ($G_{minimum}$) or ($G_{maximum}$) will lead to major errors in the determination of the parallel conductance.

The application of the conductance method in blood vessels involves an additional problem. Since blood can be considered to be a suspension of small insulating particles (blood cells) in a conductive fluid (plasma), and blood flows more quickly in the centre of the blood vessel than near the wall of the blood vessel, the blood cells will be exposed to different shearing forces during the cardiac cycle. This will cause the blood cells to change their orientation and to deform when the cardiac output increases, as a result of which the effective path length of an electron current will become smaller and the electrical conductivity of the blood will increase. The reverse takes place when the cardiac output decreases. This results in a pulsating change in the conductivity of the blood at constant cross-sectional dimensions and a constant parallel conductance. It is for this reason that the application of the conductance method for determining the cross-sectional dimensions of a blood vessel has not been accepted so far.

SUMMARY OF THE INVENTION

The object of the invention is to provide a method and apparatus of the kind referred to in the introduction, wherein the objections that stand in the way of using the aforesaid conductance method have been overcome in a simple yet efficient manner.

To this end, the method according to the invention is characterized in that an injected quantity of indicator is determined and the development of the concentration of this indicator in the blood is measured, wherein the cardiac output is calculated from the injected quantity of indicator and the development of the concentration thereof, and wherein the segmental volume and electrical parallel conductance of a cardiac chamber or a blood vessel are calculated from the calculated cardiac output, the injected quantity of conductance indicator and the measured conductance.

The apparatus for determining the segmental volume of a cardiac chamber or a blood vessel of a patient, which comprises a processing unit having a control output for initiating the injection of a first indicator into the bloodstream of the patient, which influences the conductance of the blood, a first detector to be placed in a cardiac chamber or blood vessel for measuring a conductance signal, which depends on the electrical conductance at the location of the detector, wherein said processing unit is arranged for calculating the segmental volume of the cardiac chamber or the blood vessel from said conductance signal, is according to the invention characterized by a second detector to be placed in the bloodstream for measuring an indicator signal depending on a concentration of indicator in the blood, wherein said processing unit is arranged for calculating the cardiac output from the injected quantity of indicator and the indicator signal, and calculating the segmental volume and electrical parallel conductance of a cardiac chamber or a blood vessel from the calculated cardiac output, the injected quantity of conductance indicator and the conductance signal.

The method and apparatus according to the invention enable a double indicator measurement, wherein one measurement is carried out to measure the cardiac output in the same manner as with a thermodilution method, which is known per se, and the other measurement is used to measure, similarly to the thermodilution method, the dilution of the number of ions, as it were, following the injection of, for example, a hypertonic saline solution or a hypotonic glucose solution. Since only the average change in the electrical conductance over the heartbeats is measured, pulsating changes in the shearing rate on the blood cells and in the electrical conductance of the tissues surrounding the blood do not influence the segmental volume to be calculated or the cross-sectional dimensions to be calculated therefrom. Moreover, it is possible to determine the parallel conductance by determining an area under the conductance dilution curve following the injection of a saline solution.

BRIEF DESCRIPTION OF THE DRAWINGS

The invention will now be explained in more detail with reference to the drawings, which schematically show an exemplary embodiment of the apparatus according to the invention.

DETAILED DESCRIPTION OF THE ILLUSTRATIVE EMBODIMENTS SUMMARY OF THE INVENTION

Figure 1:
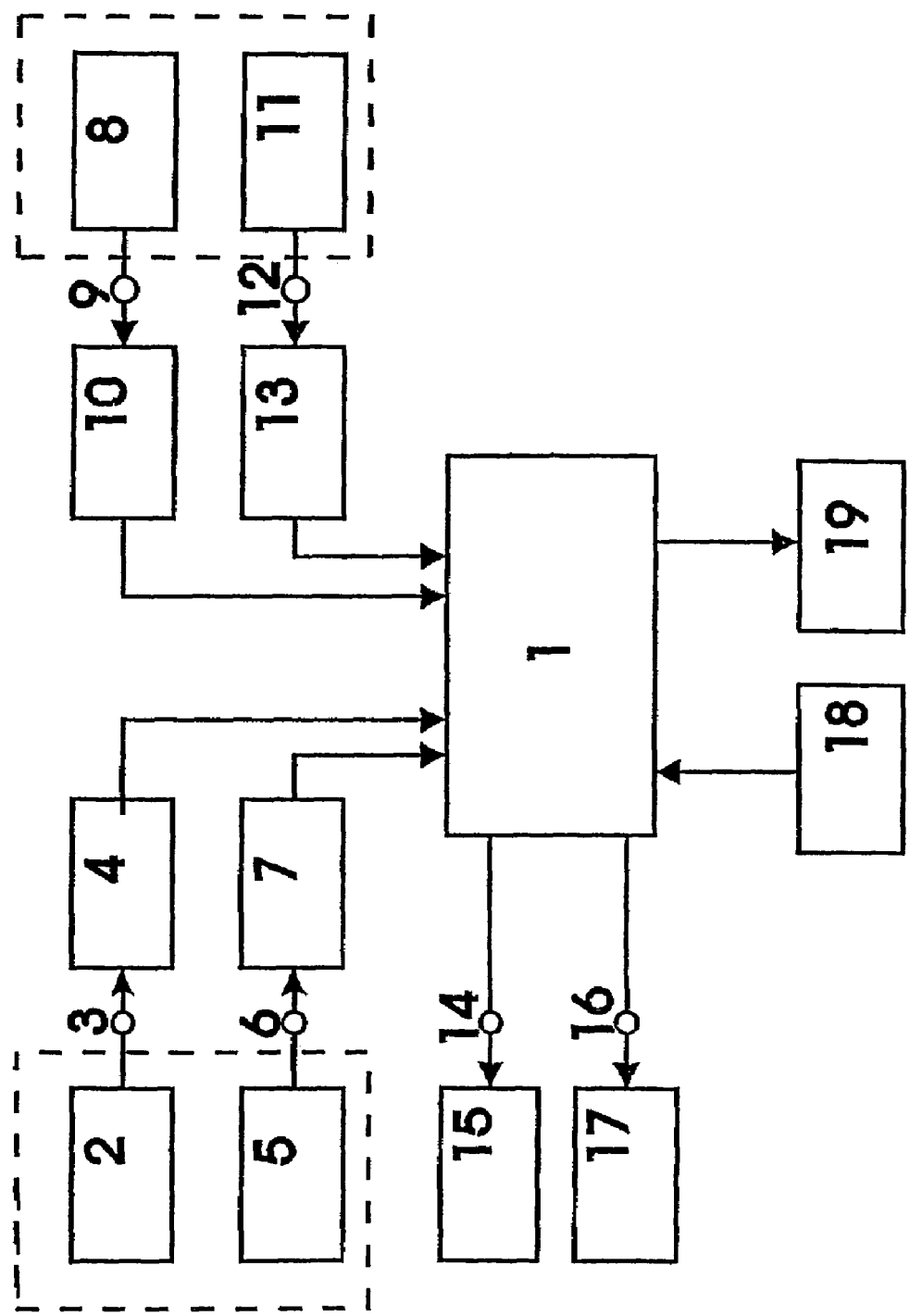
FIG. 1 is a block diagram of a possible embodiment of the apparatus according to the invention.

FIG. 1 shows a strongly simplified block diagram of the apparatus for determining the volume and the electrical parallel conductance of a cardiac chamber or a blood vessel of a patient. Said apparatus comprises a processing unit 1, which includes one or two control outputs 14 and 16, by means of which the processing unit 1 is capable of controlling one or two injection devices 15 and 17 (schematically shown), by means of which an indicator can be injected into the bloodstream of the patient. It is noted that alternatively said control outputs can also deliver a signal to initiate the injection of an indicator, whereby the indicator is injected by a doctor or other qualified person.

Figure 3:
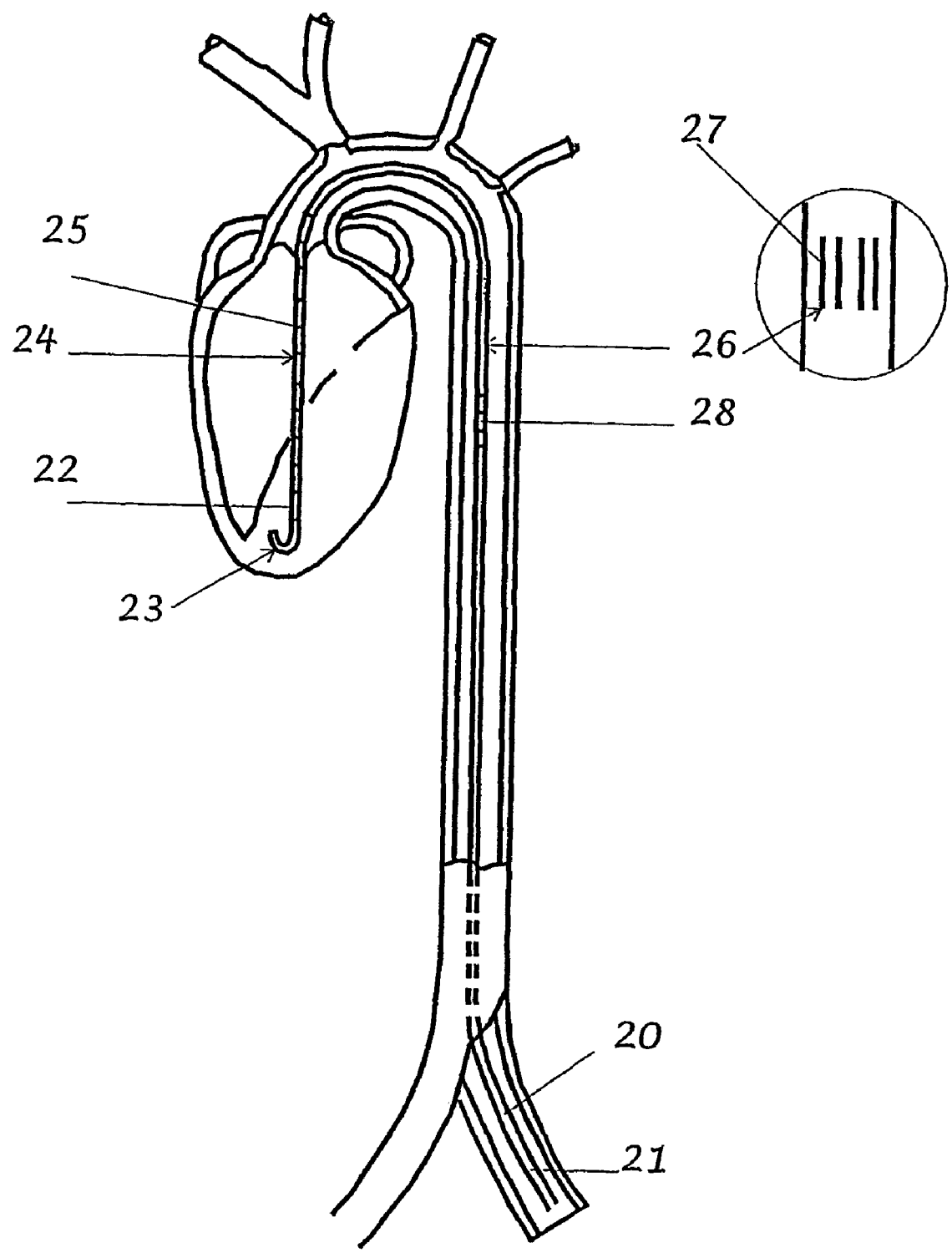
FIG. 3 shows an example of a catheter according to the invention.

For said injection a thermodilution catheter and an electrical conductance catheter, for example, or a special catheter as shown in FIG. 3, are introduced into the bloodstream of a patient in a usual manner. The catheter according to FIG. 3 will be described in more detail yet. One or two indicators will be injected via one of said catheters. The indicator that is used for determining the cardiac output can be a cold fluid, a colorant, a saline solution, a glucose solution or the like, for example. The indicator that is used for determining the conductance can be a saline solution or a glucose solution, for example. It is possible to combine the indicators used for the two measurements to provide one indicator, for example a cold or a coloured saline solution. Furthermore, it is possible to use an ordinary saline solution, wherein the development of the conductance of the blood in the direct vicinity of the detector is measured for the purpose of determining the development of the concentration so as to make it possible to determine the cardiac output.

The cathetert(s) has (have) two detectors 2 and 5 (schematically indicated), which are spaced from the injection opening by some distance. Detector 2 includes at least four, for example twelve, successive annular electrodes, and delivers a conductance signal which depends on the sum of the electrical conductance values between successive, activated annular electrodes and the parallel conductance. Detector 5 is adapted for measuring the concentration of the indicator in the blood and delivers a concentration signal. Said detector 5 is a thermistor, an optical detector or a conductivity detector, for example. Detectors 2 and 5 are connected to inputs 3 and 6 of the device. The obtained measuring signals are amplified by amplifiers 4 and 7 and fed to the inputs of processing unit 1.

In this way, so-called dilution curves can be determined, which illustrate the development of the concentration in time. From this, the cardiac output can be calculated on the basis of the known quantity of indicator that has been injected. For, the following obtains:

$$m_i = \int Q'_b(t) \cdot c(t) dt \qquad (2)$$

wherein $m_i$ is the injected quantity of indicator, $c(t)$ is the development of the concentration and $Q_b'(t)$ is the cardiac output. Given a constant cardiac output and a sudden injection of a cold fluid as the indicator, the following equation can be written:

$$Q_i \rho_i S_i (T_b - T_i) = Q'_b \rho_b S_b \int \Delta T_b(t) dt \qquad (3)$$

wherein $Q_i$ is the injection volume, $\rho$ is the specific heat and $S$ is the specific mass of the injected indicator (i) and of blood (b), respectively, $T$ is the temperature, $Q'_b$ is the cardiac output and $\Delta T_b$ is the change in the temperature of the blood that is brought about by the injection of a cold fluid.

Rearrangement of the equation shows how the cardiac output can be calculated:

$$Q'_b = Q_i \frac{\rho_i S_i (T_b - T_i)}{\rho_b S_b \int \Delta T_b(t) dt} \qquad (4)$$

This equation forms the basis for most thermodilution "cardiac output" computers.

For a hypertonic saline solution as the indicator for example, equation 3 can be rewritten to give:

$$Q_i (\sigma_i - \sigma_b) = Q'_b \int \Delta \sigma_b(t) dt \qquad (5)$$

wherein $\sigma_i$ is the conductivity of the injected indicator and $\sigma_b$ is the conductivity of blood.

Rewriting of equation 1 for the change of the conductivity of blood $\Delta \sigma_b$, gives:

$$\Delta \sigma_b(t) = \Delta G(t) \frac{L^2}{Q_{seq}} \qquad (6)$$

Combination of equations 5 and 6 results in:

$$Q_{seg} = \frac{Q'_b}{Q_i} \frac{L^2}{(\sigma_i - \sigma_b)} \int \Delta G(t) dt \qquad (7)$$

$\sigma_b$ and $\sigma_i$ are measured by means of a measuring cell which is known per se, in which detectors for temperature 8 and conductivity 11 are housed. Said detectors 8 and 11 are connected to the inputs 9 and 12 of the device. The obtained measuring signals are amplified by amplifiers 10 and 13, and fed to the processing unit 1. If detector 5 is adapted for measuring the conductivity of the blood, $\sigma_b$ can possibly be measured by means of detector 5. The values for $\sigma_b$ and $\sigma_i$ can also be input via an input device 18. The signals are converted by the processing unit 1 into values that obtain for the blood temperature as measured by detector 2. Since $\sigma_i$ is more than 25 times as large as $\sigma_b$ (in the case of a 3M hypertonic saline solution), $\sigma_b$ can generally be disregarded.

From the above it follows that it is possible, using a combined injection of a single cold hypertonic saline solution, to determine the segmental volume between two successive annular electrodes, or the cross-sectional dimensions, of a cardiac chamber or a blood vessel. The influence of the shearing rates on the blood cells is thus eliminated.

With regard to the electrical parallel conductance, another reasoning can be followed. Equation 1 can be rewritten as follows:

$$G_p = G(t) - Q_{seg}(t)\frac{\sigma_b}{L^2} \qquad (8)$$

Combination of $Q_{seg}$ of equation 7 with equation 8 gives:

$$G_p = G_{mean}(t) - \frac{Q'_b \sigma_b}{Q_i \sigma_i} \int \Delta G(t) dt \qquad (9)$$

wherein $G_{mean}$ (t) is the average value of the measured conductance over one heartbeat for the injection of a saline solution (indicated at 30 in FIG. 2) and $\Delta G(t)$ is the change in the measured conductance per heartbeat that results from the injection of the saline solution. This change is reflected in FIG. 2A. Once the parallel conductance $G_p$ has been determined in this manner, the segmental volume of the cardiac chamber and thus the heart function can be measured continuously by means of the conductance signal of detector 2, wherein the processing unit 1 determines the segmental volume with the calculated value Gp as the correction value from equation 1.

In order to monitor the segmental volume and the electrical parallel conductance within the cardiac cycle, the conductance signal must be divided into i equal intervals for every cardiac cycle during the passage of the indicator. The first interval is at the beginning of the systole and the $i^{th}$ interval is at the end of the diastole. For every $i^{th}$ interval, the conductance signal is averaged for every heartbeat. Said measuring points form an indicator dilution curve, from which the segmental volume and the parallel conductance for said $i^{th}$ interval can be calculated in accordance with equation 7 and equation 9, respectively.

Figure 2:
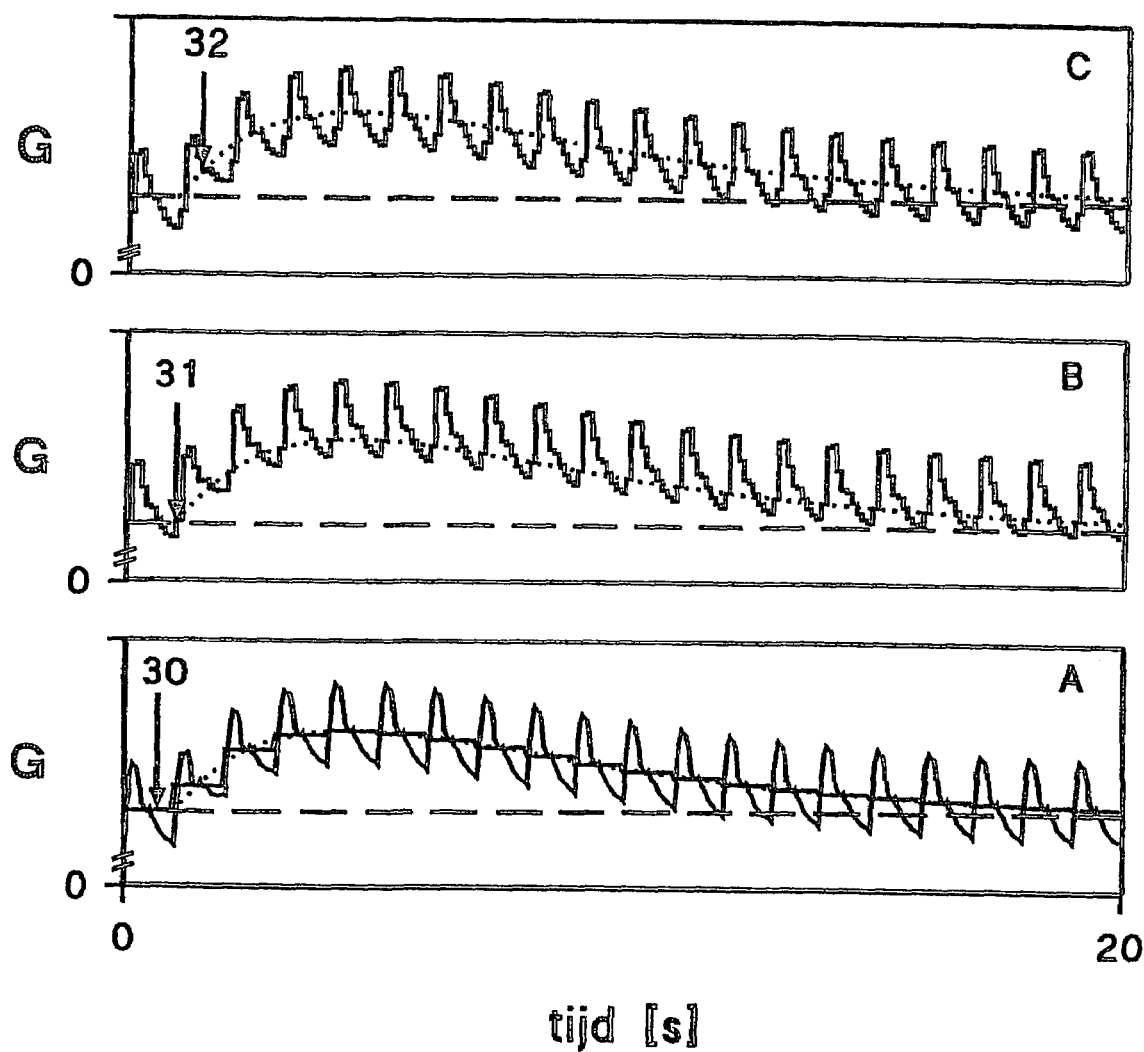
FIG. 2 schematically shows a few diagrams of the processing of the electrical conductance signal.

This principle of operation is shown in FIG. 2; for one interval per cardiac cycle (in A); for the first time interval 31 of, for example, ten intervals per cardiac cycle (in B); and for the sixth time interval 32 of said ten intervals per cardiac cycle (in C).

FIG. 3 schematically shows a catheter 20 that can be used with the method and apparatus described herein. Catheter 20 comprises a lumen 21 provided with outlet openings 22 near the distal end 23 of the catheter. Via said lumen 20, the indicator(s) can be injected into the cardiac chamber of the blood vessel. Furthermore, a conductance detector 24 is provided near said distal end 23, which detector comprises twelve annular electrodes 25 in the illustrated embodiment. A concentration detector 26 is provided some distance away from said distal end 23, which detector, in the illustrated embodiment thereof, comprises four parallel electrodes 27, by means of which the conductivity of the adjacent blood can be measured. Electrodes 27 preferably extend in axial direction on part of the circumference of the catheter. This makes it possible to place the catheter 20 in the blood vessel in such a manner that the electrodes 27 will be clear of the wall of the blood vessel at all times. It is noted that the detector 26 can also be in the form of a thermistor.

Catheter 20 may comprise a second conductance detector 28, if desired, which is spaced from the distal end 23 by such a distance that said detector will be positioned in the aorta if the detector 24 is positioned in the cardiac chamber. This makes catheter 20 suitable for measuring the segmental volume and the parallel conductance of a blood vessel and the cardiac chamber.

In an alternative embodiment of the catheter not shown, the concentration detector 26, and possibly the second conductance detector 28, may be positioned closer to the distal end of the catheter than the conductance detector 24.

It is noted that all (measuring) results can be displayed on a suitable display device 19 in a manner that is known per se.

The invention is not restricted to the embodiments as described above, which can be varied in several ways without departing from the scope of the invention as defined in the claims.

The invention claimed is:

1. A method for determining the segmental volume and the electrical parallel conductance of a cardiac chamber or a blood vessel of a patient, the method comprising:
    injecting a conductance indicator, which influences electrical conductance of blood, into a bloodstream of a patient, wherein an injected quantity of the conductance indicator is determined;
    measuring the electrical conductance in said cardiac chamber or blood vessel;
    calculating a sum of segmental volume of said cardiac chamber or blood vessel and electrical parallel conductance from said measured electrical conductance;
    measuring development of concentration of a concentration indicator in the bloodstream;
    calculating the cardiac output from the injected quantity of concentration indicator and the development of the concentration thereof; and
    calculating the segmental volume and the electrical parallel conductance of the cardiac chamber or the blood vessel from the calculated cardiac output, the injected quantity of conductance indicator and the measured electrical conductance.

2. The method according to claim 1, wherein the conductance indicator comprises the concentration indicator, and wherein measuring the development of the concentration comprises measuring the temperature or the color of the concentration indicator.

3. The method according to claim 1, and further comprising injecting the concentration indicator.

4. The method according to claim 1, and further comprising:
    using the calculated parallel conductance a correction value; and
    determining the segmental volume exclusively from the conductance signal using said correction value.

5. The method according to claim 1, and further comprising:
    dividing a period of a heartbeat into equal time segments; and monitoring continuously the segmental volume and the electric parallel conductance of the cardiac chamber or the blood vessel within the for multiple heartbeat.

6. An apparatus for determining a segmental volume of a cardiac chamber or a blood vessel of a patient, the apparatus comprising:
- a processing unit having a control output for initiating injection of a conductance indicator into a bloodstream of the patient, which influences electrical conductance of blood;
- a first detector configured to be placed in the cardiac chamber or blood vessel for measuring a conductance signal, which depends on the electrical conductance at the location of the first detector, wherein said processing unit is arranged for calculating the segmental volume of the cardiac chamber or the blood vessel from said conductance signal;
- a second detector configured to be placed in the bloodstream for measuring an indicator signal depending on a concentration of a concentration indicator in the blood, wherein said processing unit is arranged for calculating the cardiac output from an injected quantity of the conductance indicator and the indicator signal, and calculating the segmental volume and electrical parallel conductance of the cardiac chamber or blood vessel from the calculated cardiac output, the injected quantity of conductance indicator and the conductance signal.

7. The apparatus according to claim 6, wherein the conductance indicator comprises the concentration indicator and wherein said second detector is adapted for measuring the concentration of said conductance indicator.

8. The apparatus according to claim 6, wherein the conductance indicator is different than the concentration indicator, and wherein said control output initiates the injection of the concentration indicator.

9. The apparatus according to claim 6, and further comprising at least one injector, wherein said control output controls said at least one injector device for injecting at least one of the conductance indicator and the concentration indicator.

10. The apparatus according to claim 6, wherein said processing unit uses the calculated parallel conductance as a correction value for determining the segmental volume exclusively from said conductance signal.

11. The apparatus according to claim 6, wherein said first and said second detectors are housed in a common catheter.

12. The apparatus according to claim 11, wherein said catheter also includes a lumen for injecting at least one of the conductance indicator and the concentration indicator.

13. A catheter for determining segmental volume and electrical parallel conductance of a cardiac chamber or a blood vessel of a patient, the catheter comprising:
- a first detector configured for measuring a conductance signal depending on electrical conductance of blood;
- a second detector configured for measuring an indicator signal depending on a concentration of a concentration indicator in the blood, wherein said first detector is positioned closer to a distal end than said second detector; and
- a third detector corresponding to said first detector, which third detector is spaced from said distal end by such a distance so that the third detector is adapted to be positioned in an aorta when said first detector is positioned in a heart.

14. The catheter according to claim 13, wherein said second detector comprises a number of parallel electrodes, which are axially provided on the catheter.

15. The catheter according to claim 13, wherein the catheter includes a lumen comprising at least one outlet opening between said first detector and said distal end.

16. The catheter of claim 13, wherein the third detector is a conductance detector.

* * * * *